(12) United States Patent
Huh

(10) Patent No.: US 11,033,434 B2
(45) Date of Patent: Jun. 15, 2021

(54) WELDING HELMET

(71) Applicant: OTOS WING.CO., LTD., Seoul (KR)

(72) Inventor: Moon Young Huh, Seoul (KR)

(73) Assignee: OTOS WING.CO., LTD., Seoul (KR)

( * ) Notice: Subject to any disclaimer, the term of this patent is extended or adjusted under 35 U.S.C. 154(b) by 0 days.

(21) Appl. No.: 16/554,451

(22) Filed: Aug. 28, 2019

(65) Prior Publication Data

US 2020/0113739 A1  Apr. 16, 2020

(30) Foreign Application Priority Data

Oct. 15, 2018 (KR) .................. 10-2018-0122768

(51) Int. Cl.
| | |
|---|---|
| *A61F 9/06* | (2006.01) |
| *H02J 7/00* | (2006.01) |
| *G02F 1/133* | (2006.01) |
| *A42B 3/22* | (2006.01) |
| *A42B 3/00* | (2006.01) |
| *G02F 1/137* | (2006.01) |

(52) U.S. Cl.
CPC .............. *A61F 9/067* (2013.01); *A42B 3/006* (2013.01); *A42B 3/225* (2013.01); *G02F 1/13318* (2013.01); *H02J 7/0063* (2013.01); *G02F 1/137* (2013.01); *G02F 1/13312* (2021.01); *G02F 1/13324* (2021.01); *Y02B 70/10* (2013.01)

(58) Field of Classification Search
CPC .................... Y02B 70/16; G06F 1/26
See application file for complete search history.

(56) References Cited

U.S. PATENT DOCUMENTS

| | | | | |
|---|---|---|---|---|
| 2012/0236613 | A1* | 9/2012 | Chen | ........................ G06F 1/26 |
| | | | | 363/126 |
| 2016/0329183 | A1* | 11/2016 | Estevez | .............. H01H 59/0009 |
| 2018/0360663 | A1* | 12/2018 | Hsieh | .................. G02F 1/13471 |

FOREIGN PATENT DOCUMENTS

| | | | |
|---|---|---|---|
| CN | 201719439 U | * | 1/2011 |
| KR | 10-0381547 B1 | | 4/2003 |
| KR | 10-1163420 B1 | | 7/2012 |

* cited by examiner

*Primary Examiner* — Alexander P Gross
(74) *Attorney, Agent, or Firm* — Kilpatrick Townsend & Stockton LLP

(57) ABSTRACT

Provided is a welding helmet maintaining a power-on state after initial power is applied thereto, the welding helmet including: a circuit unit controlling a shutter liquid crystal display (LCD) based on at least one of whether welding light exists and an intensity of the welding light; a power supply unit supplying power to the circuit unit; and a switch unit controlling electrical connection between the circuit unit and the power supply unit, wherein after being initially switched to an on state, the switch unit maintains the on state.

5 Claims, 7 Drawing Sheets

WELDING HELMET

CROSS-REFERENCE TO RELATED APPLICATION

This application claims the benefit of Korean Patent Application No. 10-2018-0122768, filed on Oct. 15, 2018, in the Korean Intellectual Property Office, the disclosure of which is incorporated herein in its entirety by reference.

BACKGROUND

1. Field

One or more embodiments relate to welding helmets, and more particularly, to welding helmets that may maintain a power-on state after initial power is applied thereto.

2. Description of Related Art

In general, welding is an operation of joining two metals together by locally heating and melting metal by using the fusibility of metal. In such a welding operation, because high-temperature and high-brightness light and gas are generated, an operator (e.g., a welder) wears a welding helmet as an item of protection equipment.

In the case of a manual-type welding helmet according to the related art, an operator is inconvenienced by having to frequently repeat an operation of holding and releasing a handle of the welding helmet in a welding operation. Thus, some related art has proposed a band-type welding helmet capable of being fixed to the head of an operator, to improve the above manual-type welding helmet.

A welding helmet is used to protect the face and eyes of an operator during an operation such as welding or cutting. Also, the welding helmet is equipped with an anti-glare device (hereinafter referred to as a "cartridge") for protecting the user's eyes from intense harmful light generated during an operation such as welding or cutting.

In general, the cartridge may block rays with wavelengths of 780 nm or more and less than 365 nm and control the transmission of visible rays, thus allowing the user to perform a welding operation while visually identifying a welding position without glare.

Meanwhile, when the user of the welding helmet performs a welding operation in a state of having forgotten to turn on the power thereof (i.e., in a state where the above cartridge does not operate), the user may suffer serious damage such as damage to optic nerves due to the characteristics of a welding operation.

Thus, it may be desirable for the power to the welding helmet to be normally supplied even when the user forgets to turn on the power; however, when the welding helmet has power distributed thereto from the power applied from the manufacturing time thereof, the user may receive the welding helmet in a discharged or nearly-discharged state in some cases.

SUMMARY

One or more embodiments include welding helmets in which power may be normally supplied after power is initially applied.

One or more embodiments include welding helmets that may efficiently manage power by blocking normally-supplied power after a lapse of a certain time.

Additional aspects will be set forth in part in the description which follows and, in part, will be apparent from the description, or may be learned by practice of the presented embodiments of the disclosure.

According to one or more embodiments, a welding helmet maintaining a power-on state after initial power application thereto includes: a circuit unit controlling a shutter liquid crystal display (LCD) based on at least one of whether welding light exists and an intensity of the welding light; a power supply unit supplying power to the circuit unit; and a switch unit controlling electrical connection between the circuit unit and the power supply unit, wherein after being initially switched to an on state, the switch unit maintains the on state.

Before being initially switched to the on state, the switch unit may maintain an off state to block the electrical connection between the circuit unit and the power supply unit.

The switch unit may include: a first switch unit controlling connection between the circuit unit and the power supply unit; a second battery providing a voltage for maintaining an off state of the first switch unit; a user operation unit switching a voltage of an input terminal for switching a state of the first switch unit, from the voltage of the second battery to a reference voltage in response to a user's startup operation; and a second switch unit maintaining the voltage of the input terminal at the reference voltage based on a control signal of the circuit unit after the switch unit is initially switched to the on state, wherein the first switch unit may be in an on state when the voltage of the input terminal is the reference voltage.

The circuit unit may include a controller controlling the shutter LCD. The controller may output a control signal for maintaining the on state of the switch unit to the switch unit when power is applied by the power supply unit.

The controller may stop the outputting of the control signal when a certain time has elapsed from the time of starting to output the control signal. The switch unit may be switched to an off state to block the electrical connection between the circuit unit and the power supply unit when the outputting of the control signal is stopped by the controller.

These and/or other aspects, features, and advantages will become apparent from the accompanying drawings, the appended claims, and the following detailed description of the present disclosure.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
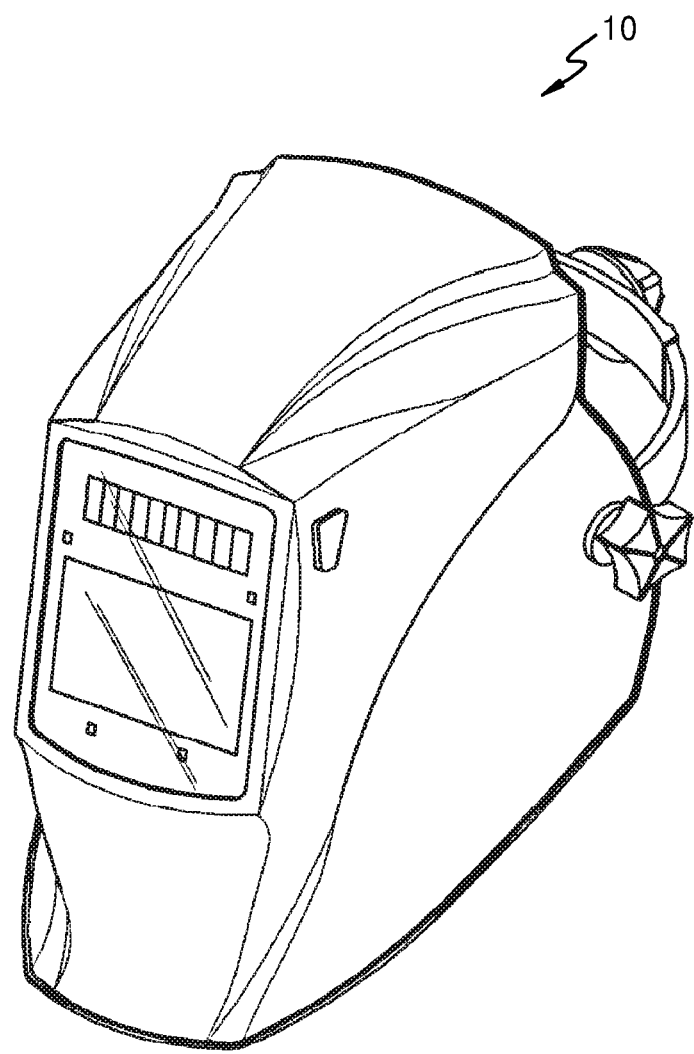
FIG. 1 is a perspective view illustrating an appearance of a welding helmet according to an embodiment of the present disclosure.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Hereinafter, embodiments of the present disclosure will be described in detail with reference to the accompanying drawings, and in the following description, like reference numerals will denote like elements and redundant descriptions thereof will be omitted.

It will be understood that although terms such as "first" and "second" may be used herein to describe various components, these components should not be limited by these terms and these terms are only used to distinguish one component from another component. As used herein, the singular forms "a", "an", and "the" are intended to include the plural forms as well, unless the context clearly indicates otherwise. It will be understood that terms such as "comprise", "include", and "have" used herein specify the presence of stated features or components, but do not preclude the presence or addition of one or more other features or components. Sizes of components in the drawings may be exaggerated for convenience of description. In other words, because the sizes and shapes of components in the drawings are arbitrarily illustrated for convenience of description, the present disclosure is not limited thereto.

Figure 2:
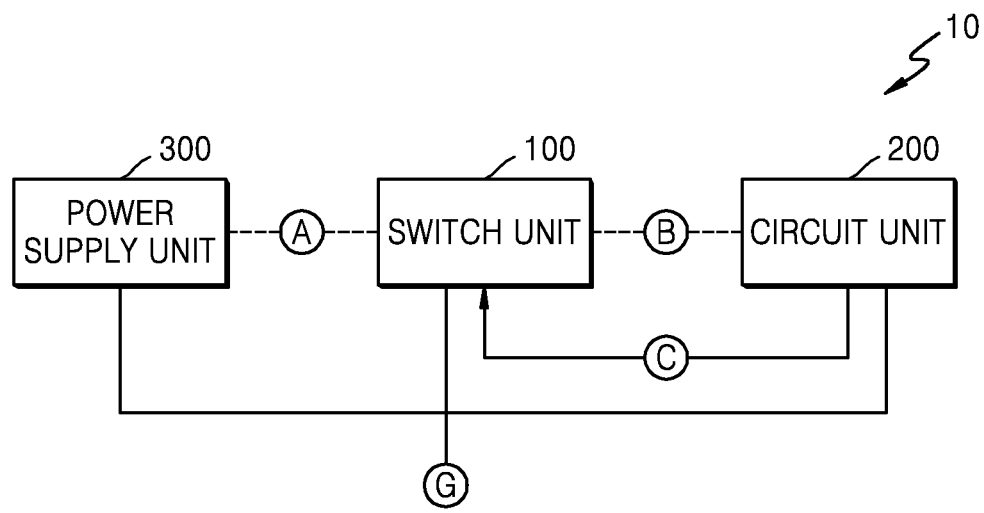
FIG. 2 is a diagram schematically illustrating a configuration of a welding helmet according to an embodiment of the present disclosure.
Figure 3A:
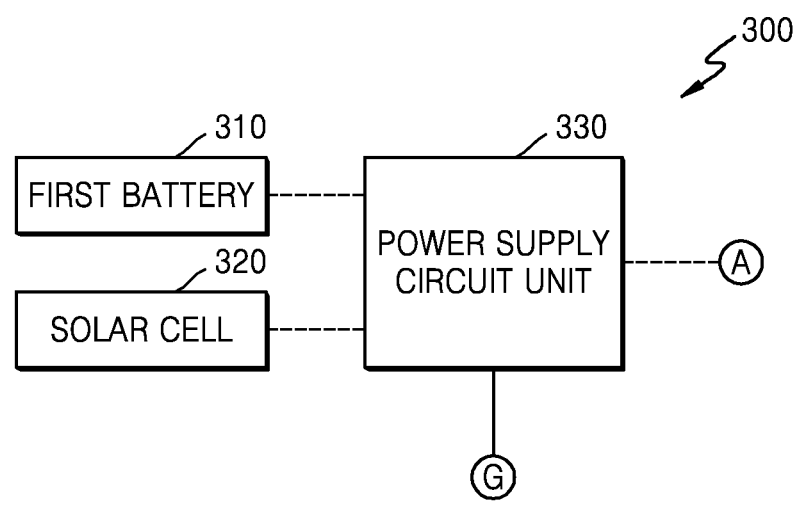
FIGS. 3A, 3B, and 3C are diagrams illustrating in detail the respective configurations of a welding helmet according to an embodiment of the present disclosure.
Figure 3B:
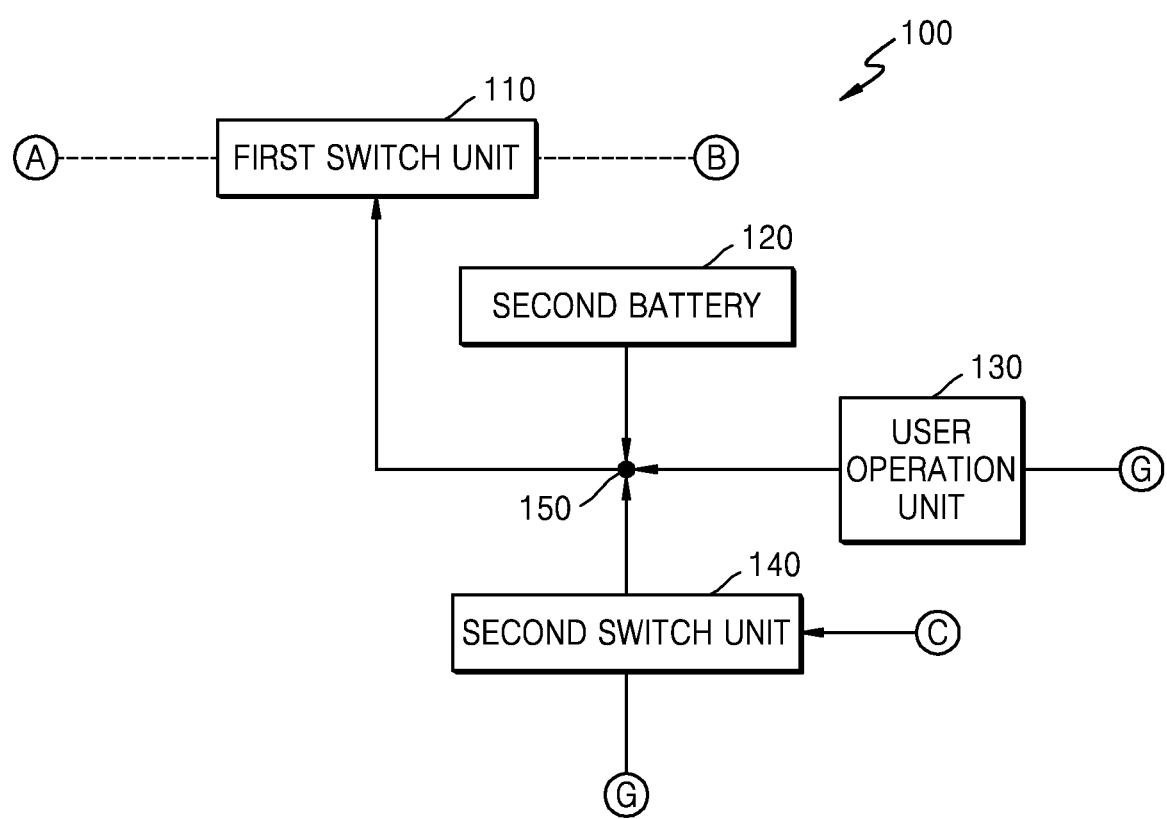
Figure 3C:
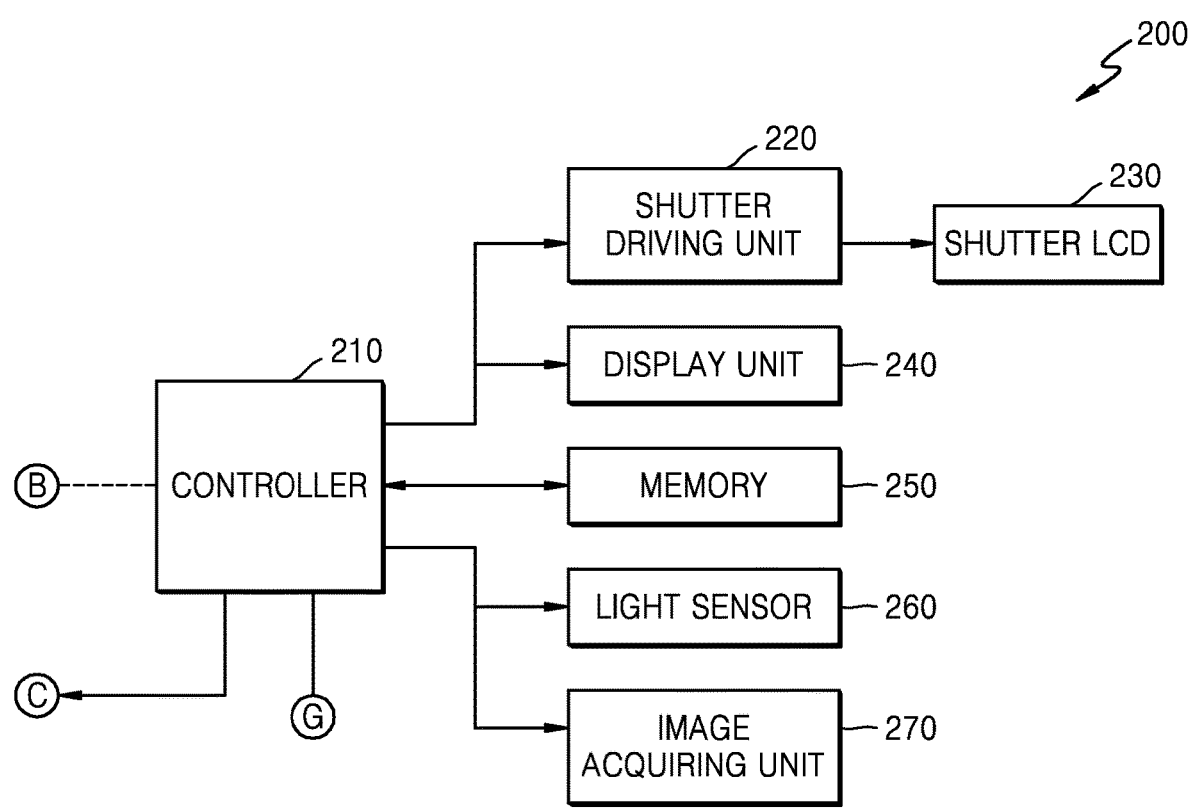

FIG. 1 is a perspective view illustrating an appearance of a welding helmet 10 according to an embodiment of the present disclosure, and FIG. 2 is a diagram schematically illustrating a configuration of a welding helmet according to an embodiment of the present disclosure. Also, FIGS. 3A, 3B, and 3C are diagrams illustrating in detail the respective configurations of a welding helmet according to an embodiment of the present disclosure. Hereinafter, descriptions will be given with reference to FIGS. 1 to 3C.

A welding helmet 10 according to an embodiment of the present disclosure may protect the face and eyes of an operator (e.g., a welder) by controlling a shutter liquid crystal display (LCD) based on at least one of whether welding light exists and the intensity of the welding light.

The welding helmet 10 may include a housing illustrated in FIG. 1, a switch unit 100, a circuit unit 200, and a power supply unit 300 arranged in the housing. In this case, the housing may include nonflammable lightweight material such as nonflammable plastic.

The power supply unit 300 according to an embodiment of the present disclosure may be to supply power to the circuit unit 200 according to the operation of the switch unit 100 and may include a first battery 310, a solar cell 320, and a power supply circuit unit 330.

The first battery 310 may mean an electric energy storage unit that temporarily store electric energy (or power) and supplies the electric energy (or power) to the circuit unit 200 when necessary. For example, the first battery 310 may include a lithium-ion battery pack including at least one lithium-ion cell and a battery management system (BMS) for managing the at least one lithium-ion cell.

The solar cell 320 may mean an energy conversion unit for converting welding light and/or sunlight into electric energy. The electric energy generated by the solar cell 320 may be stored in the first battery 310 described above or may be used for the operation of the circuit unit 200.

The power supply circuit unit 330 may supply the circuit unit 200 with the electric energy provided by the first battery 310 and/or the solar cell 320 described above. In this case, the power supply circuit unit 330 may suitably adjust the voltage of the electric energy provided by the first battery 310 and/or the solar cell 320, according to the rated voltage of the circuit unit 200.

In an alternative embodiment, the power supply circuit unit 330 may transmit the electric energy generated by the solar cell 320 to the first battery 310, to charge the first battery 310.

The circuit unit 200 according to an embodiment of the present disclosure may be to control a shutter LCD 230 based on at least one of whether welding light exists and the intensity of the welding light and may include a controller 210, a shutter driving unit 220, a shutter LCD 230, a display unit 240, a memory 250, a light sensor 260, and an image acquiring unit 270.

The controller 210 according to an embodiment of the present disclosure may control the shutter LCD 230 based on at least one of whether welding light exists and the intensity of the welding light.

Also, when power is initially applied by the power supply unit 300 described above, the controller 210 may generate a control signal for maintaining the switch unit 100 in an on state to maintain the power supply by the power supply unit 300 and output the generated control signal to the switch unit 100.

Also, the controller 210 may control other components of the welding helmet (such as the light sensor 260 and the image acquiring unit 270).

The controller 210 may include any type of device such as a processor that may process data. Here, the processor may refer to, for example, a data processing device that is embedded in hardware and has a physically structured circuit to perform a function represented by the commands or code in a program. As an example, the data processing device embedded in hardware may include any processing device such as a microprocessor, a central processing unit (CPU), a processor core, a multiprocessor, an application-specific integrated circuit (ASIC), or a field programmable gate array (FPGA); however, the present disclosure is not limited thereto.

The shutter driving unit 220 according to an embodiment of the present disclosure may vary the blackening density of the shutter LCD 230 according to the user's operation and/or the control of the controller 210 described above. In this case, the shutter LCD 230 may be a unit for suitably adjusting the welding light reaching the user's face and/or the user's eyes.

For example, as for strong welding light, the controller 210 may receive a signal corresponding to the strong welding light from the light sensor 260 described below and output a control signal for changing the blackening density of the shutter LCD 230 into high to the shutter driving unit 220 in response thereto.

The display unit 240 according to an embodiment of the present disclosure may display, for example, the result from the user's operation and/or the operation state of the welding helmet 10. For example, the display unit 240 may display accumulated work time or the like.

The memory 250 according to an embodiment of the present disclosure may store, for example, the welding strength, the welding time, the idle time, and the welding count determined by the controller 210. The memory 250 may store an image about the welding state acquired by the image acquiring unit 270 described below. Also, the memory 250 may store source code and/or software for driving the controller 210 described above. The memory 250 may include magnetic storage media or flash storage media; however, the present disclosure is not limited thereto.

The light sensor 260 according to an embodiment of the present disclosure may detect whether welding light exists and/or the intensity of the welding light and transmit the detection result to the controller 210.

The image acquiring unit 270 according to an embodiment of the present disclosure may acquire an image about the welding state.

The switch unit 100 according to an embodiment of the present disclosure may be to control the electrical connection between the circuit unit 200 and the power supply unit 300 according to the user's operation and/or the control of the controller 210 and may include a first switch unit 110, a second battery 120, a user operation unit 130, a second switch unit 140, and an input terminal 150 for switching the state of the first switch unit 110.

The first switch unit 110 according to an embodiment of the present disclosure may control the electrical connection between the circuit unit 200 and the power supply unit 300 according to the user's operation and/or the control of the controller 210. The first switch unit 110 may include any one of a field effect transistor (FET), a bipolar junction transistor (BJT), an insulated gate bipolar transistor (IGBT), and a relay for controlling the closing/opening of the circuit according to a control signal. However, this is merely an example and the present disclosure is not limited thereto.

Meanwhile, the on/off state of the first switch unit 110 may be switched based on the voltage of the input terminal 150. For example, when the voltage of the input terminal 150 is a reference voltage (e.g., 0[V]), the first switch unit 110 may be turned on to electrically connect the circuit unit 200 to the power supply unit 300.

However, on the other hand, when the voltage of the input terminal 150 is higher than the reference voltage (e.g., the voltage of the second battery (e.g., 3[V])), the first switch unit 110 may be turned off to block the electric connection between the circuit unit 200 and the power supply unit 300. However, this operation is merely an example and the present disclosure is not limited thereto.

Meanwhile, in the present disclosure, an 'on' state of a switch unit may be a shorted state of the switch unit and may mean a state in which two contact points connected to the switch unit are electrically connected to each other. On the other hand, in the present disclosure, an 'off' state of the switch unit may be an open state of the switch unit and may mean a state in which two contact points connected to the switch unit are electrically disconnected from each other.

The second battery 120 according to an embodiment of the present disclosure may supply a voltage for maintaining the first switch unit 110 in an off state as described above. The second battery 120 may be a separate battery different from the first battery 310 described above or may be substantially the same battery as the first battery 310 described above. In an alternative embodiment, the second battery 120 may be a battery charged by the first battery 310 described above.

The user operation unit 130 according to an embodiment of the present disclosure may be to acquire a user's startup operation for initially using the welding helmet. For example, the user operation unit 130 may include a button for initial startup or may include a key-box for initial startup. However, this is merely an example and the present disclosure is not limited thereto.

Meanwhile, the user operation unit 130 may be to prevent the welding helmet 10 from becoming unusable because the first battery 310 is exhausted during the distribution of the welding helmet 10.

When the user of the welding helmet 10 performs a welding operation in a state of having forgotten to turn on the power thereof (i.e., in a state where the blackening of the shutter LCD 230 does not operate), the user may suffer serious damage such as damage to optic nerves due to the characteristics of a welding operation.

Thus, it may be desirable that the power of the welding helmet 10 is normally supplied even when the user forgets to turn on the power; however, when the welding helmet 10 is distributed with the power applied from the manufacturing time thereof, the user may receive the welding helmet 10 in a discharged state in some cases.

Accordingly, it may be necessary to normally supply power only after power is initially applied as in the welding helmet 10 according to an embodiment of the present disclosure.

The user may perform input to the user operation unit 130 at the time of initial use of the welding helmet 10 to normally supply power to the welding helmet 10, thus preventing serious damage such as damage to optic nerves caused by forgetting.

The second switch unit 140 according to an embodiment of the present disclosure may be to maintain the voltage of the input terminal 150 at a reference voltage (e.g., 0[V]) according to a control signal of the controller 210. The second switch unit 140 may include any one of a field effect transistor (FET), a bipolar junction transistor (BJT), an insulated gate bipolar transistor (IGBT), and a relay for controlling the closing/opening of the circuit according to a control signal of the controller 210. However, this is merely an example and the present disclosure is not limited thereto.

Hereinafter, with reference to FIGS. 4A to 4C, a process in which the welding helmet 10 maintains a power-on state after initial power application thereto will be described focusing on an operation of the switch unit 100. Also, for convenience of description, it is assumed that a terminal A is a terminal for connecting the power supply unit 300 to the switch unit 100, a terminal B is a terminal for connecting the switch unit 100 to the circuit unit 200, and a terminal G is a terminal for providing a reference voltage.

Figure 4A:
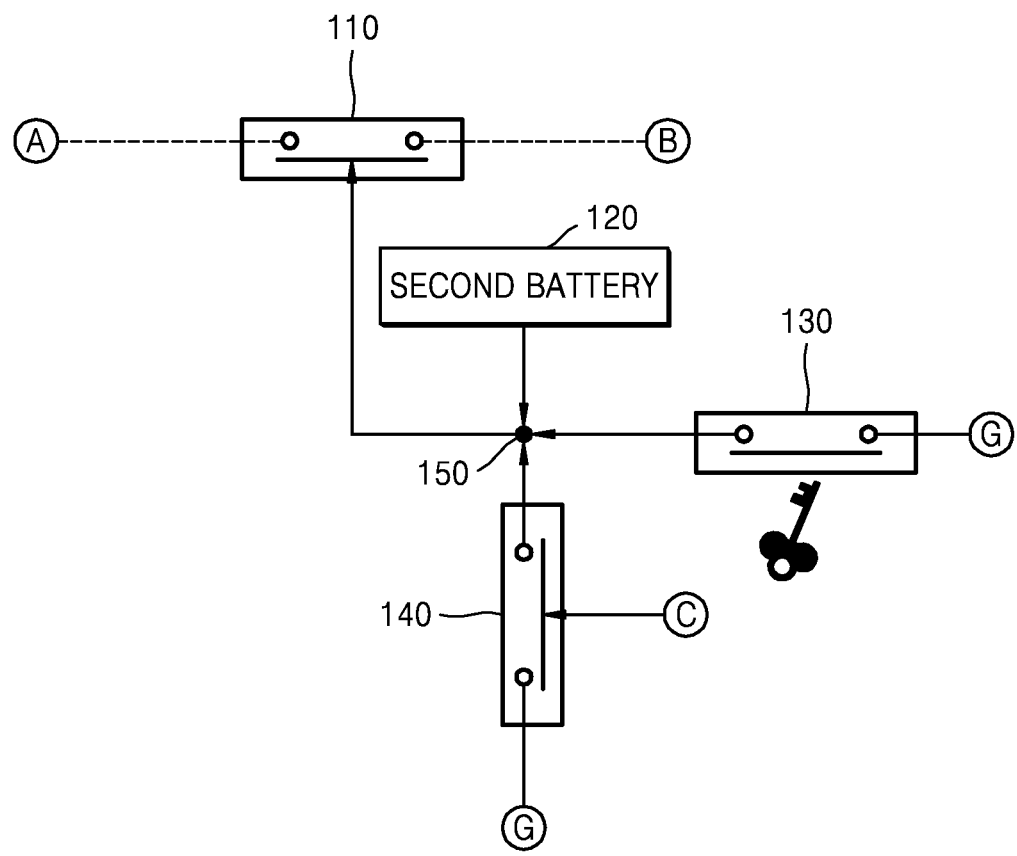
FIG. 4A is a diagram for describing an operation of a switch unit before initial power is applied to a welding helmet.

FIG. 4A is a diagram for describing an operation of the switch unit 100 before initial power is applied to the welding helmet 10.

As described above, the second battery 120 may provide a voltage for maintaining the first switch unit 110 in an off state, through the input terminal 150 of the first switch unit 110. Accordingly, the electrical connection between the power supply unit 300 and the circuit unit 200 may be blocked.

In other words, until the switch unit 100 is initially switched to an on state, the switch unit 100 may maintain the off state to block the electrical connection between the circuit unit 200 and the power supply unit 300. The voltage supplied by the second battery 120 may be higher than the reference voltage (i.e., the voltage of the G terminal G).

Meanwhile, because the electrical connection between the circuit unit 200 and the power supply unit 300 is blocked as described above, the controller 210 may not output a control signal for controlling the second switch unit 140 and thus the second switch unit 140 may maintain the off state. In this case, the off state of the second switch unit 140 may be a state in which the input terminal 150 of the first switch unit 110 and the terminal G are not electrically connected to each other.

Figure 4B:
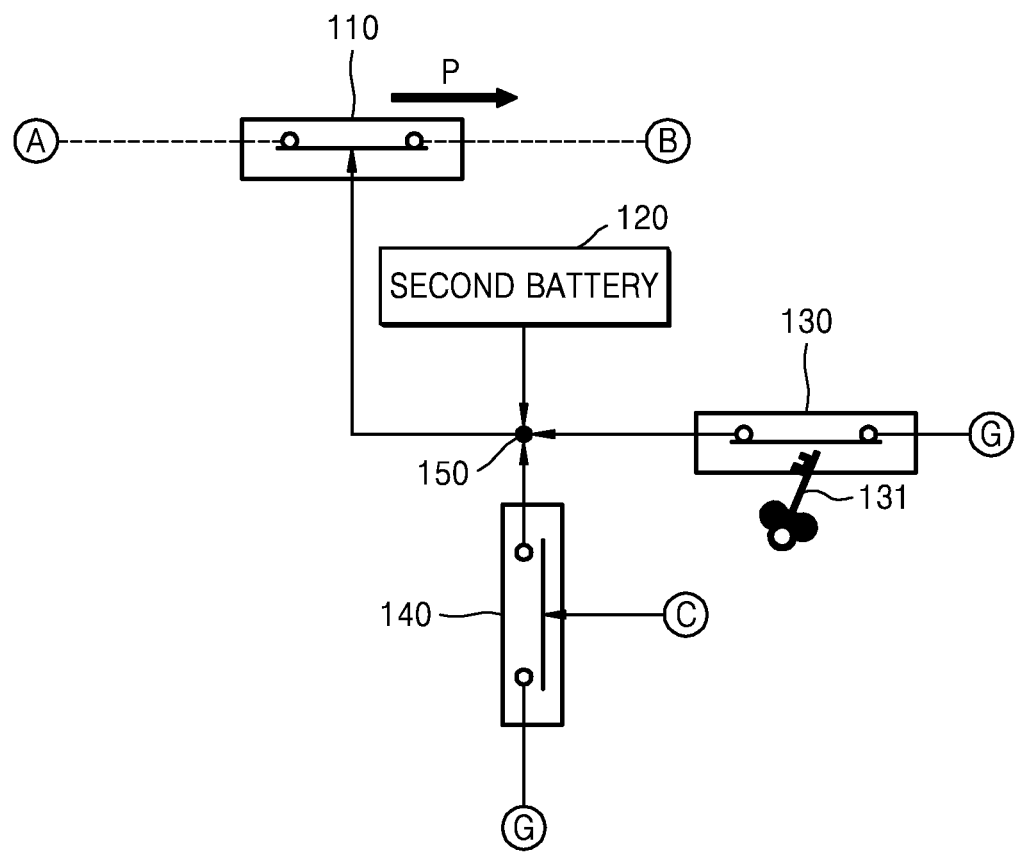
FIG. 4B is a diagram for describing an operation of a switch unit when initial power is applied to a welding helmet.

FIG. 4B is a diagram for describing an operation of the switch unit 100 when initial power is applied to the welding helmet 10.

As described above, the user operation unit 130 may be to acquire a user's startup operation for initially using the welding helmet and may be, for example, a key 131 input button for initial startup as illustrated in FIG. 4B.

By the startup operation on the user operation unit 130, the voltage of the input terminal 150 of the first switch unit 110 may be temporarily switched from the voltage of the second battery 120 to the reference voltage (i.e., the voltage of the terminal G).

Due to the switching of the voltage of the input terminal 150, the first switch unit 110 may be switched to an on state and thus the power P of the power supply unit 300 may be supplied to the circuit unit 200.

The circuit unit 200 may start operation by the supplied power P and may generate a control signal for maintaining the on state of the first switch unit 110 and output the generated control signal to the second switch unit 140.

Figure 4C:
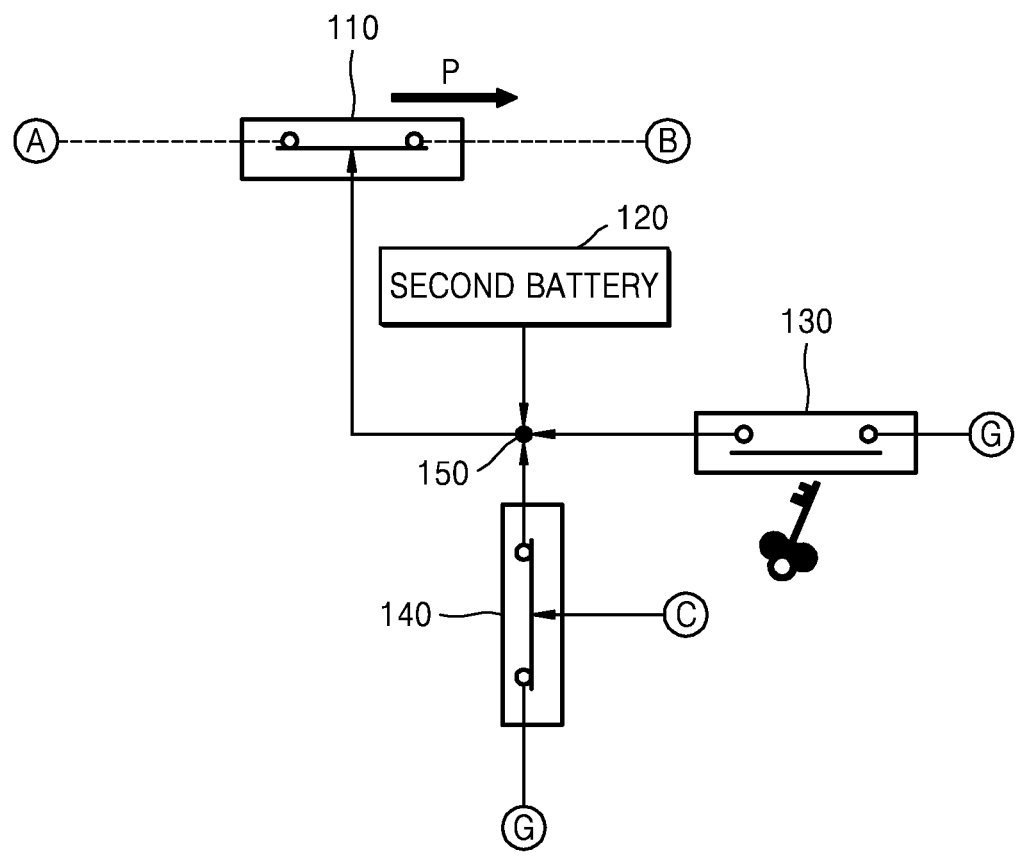
FIG. 4C is a diagram for describing an operation of a switch unit after initial power is applied to a welding helmet.

FIG. 4C is a diagram for describing an operation of the switch unit 100 after initial power is applied to the welding helmet 10.

As described above, after the initial power is applied, the circuit unit 200 may generate a control signal for maintaining the first switch unit 110 in an on state and output the generated control signal to the second switch unit 140. According to the control signal, the second switch unit 140 may maintain the voltage of the input terminal 150 of the first switch unit 110 at the reference voltage (i.e., the voltage of the terminal G). Accordingly, the welding helmet 10 according to an embodiment of the present disclosure may maintain the power-on state from a desired time of the user.

In an alternative embodiment, when a certain time has elapsed from the time of starting to output a control signal for maintaining the first switch unit 110 in the on state, the controller 210 of the circuit unit 200 according to an embodiment of the present disclosure may stop outputting the control signal.

Thus, according to the present disclosure, when the welding helmet 10 is not used for a long time, the power P supplied to the circuit unit 200 may be blocked, thereby extending the lifetime of the welding helmet 10. Meanwhile, the 'time interval' described above may be set by the user to, for example, 12 hours, 7 days, or the like.

According to the present disclosure, it may be possible to provide a welding helmet in which power may be normally supplied only after power is initially applied.

Particularly, according to the present disclosure, the user may start power supply to the welding helmet from the time of initially using the welding helmet, thereby preventing serious damage such as damage to optic nerves that may be caused by forgetting or mistaking the operation state of the welding helmet.

Also, according to the present disclosure, normally-supplied power may be blocked after a lapse of a certain time, and thus the power of the welding helmet may be efficiently managed.

Particular implementations described herein are merely embodiments, and do not limit the scope of the present disclosure in any way. For the sake of conciseness, descriptions of related art electronic configurations, control systems, software, and other functional aspects of the systems may be omitted. Also, the connection lines or connection members between various components illustrated in the drawings represent examples of functional connections and/or physical or logical connections between the various components, and various alternative or additional functional connections, physical connections, or logical connections may be present in practical apparatuses. Also, no element may be essential to the practice of the present disclosure unless the element is particularly described as "essential" or "critical".

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

What is claimed is:

1. A welding helmet maintaining a power-on state after initial power is applied thereto,
the welding helmet comprising:
a circuit unit controlling a shutter liquid crystal display (LCD) based on at least one of whether welding light exists and an intensity of the welding light;
a power supply unit supplying power to the circuit unit; and
a switch unit controlling electrical connection between the circuit unit and the power supply unit,
wherein the switch unit comprises:
a first switch unit controlling connection between the circuit unit and the power supply unit; and
a second switch unit maintaining an off state of the first switch unit before being initially switched to an on state and maintaining the on state of the first switch unit after being initially switched to the on state,
wherein the switch unit further comprises:
a second battery providing a voltage for maintaining an off state of the first switch unit; and
a user operation unit switching a voltage of an input terminal for switching a state of the first switch unit, from the voltage of the second battery to a reference voltage in response to a user's startup operation;
wherein the second switch unit maintaining the voltage of the input terminal at the reference voltage based on a control signal of the circuit unit after the switch unit is initially switched to the on state,
wherein the first switch unit is in an on state when the voltage of the input terminal is the reference voltage such that the first switch unit is initially switched to the on state when the welding helmet is initially used by a user after the welding helmet is manufactured.

2. The welding helmet of claim 1, wherein the circuit unit comprises a controller controlling the shutter LCD.

3. The welding helmet of claim 2, wherein
the controller
outputs a control signal for maintaining the on state of the switch unit to the switch unit when power is applied by the power supply unit.

4. The welding helmet of claim 3, wherein the controller stops the outputting of the control signal when a certain time has elapsed from the time of starting to output the control signal.

5. The welding helmet of claim 4, wherein the switch unit is switched to an off state to block the electrical connection between the circuit unit and the power supply unit when the outputting of the control signal is stopped by the controller.

* * * * *